United States Patent
Sur

(10) Patent No.: US 11,883,579 B2
(45) Date of Patent: *Jan. 30, 2024

(54) NO-HEAT, NO-BURN SMOKING ARTICLE

(71) Applicant: RAI Strategic Holdings, Inc., Winston-Salem, NC (US)

(72) Inventor: Rajesh Sur, Winston-Salem, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 574 days.

This patent is subject to a terminal disclaimer.

(21) Appl. No.: 17/085,415

(22) Filed: Oct. 30, 2020

(65) Prior Publication Data

US 2021/0045439 A1  Feb. 18, 2021

Related U.S. Application Data

(63) Continuation of application No. 16/719,178, filed on Dec. 18, 2019, now Pat. No. 10,856,572, which is a
(Continued)

(51) Int. Cl.
*A24F 13/00* (2006.01)
*A61M 11/00* (2006.01)
(Continued)

(52) U.S. Cl.
CPC .......... *A61M 11/005* (2013.01); *A24B 15/167* (2016.11); *A24F 40/05* (2020.01);
(Continued)

(58) Field of Classification Search
CPC ...................................................... A24F 47/00
(Continued)

(56) References Cited

U.S. PATENT DOCUMENTS

| 1,514,682 A | 11/1924 | Wilson |
| 1,771,366 A | 7/1930 | Wyss et al. |

(Continued)

FOREIGN PATENT DOCUMENTS

| AU | 276250 | 7/1965 |
| AU | 3090292 A | 6/1993 |

(Continued)

OTHER PUBLICATIONS

Ding et al., "Surface acoustic wave microfluidics", The Royal Society of Chemistry, Jul. 2013, pp. 3626-3649.
(Continued)

*Primary Examiner* — Phuong K Dinh
(74) *Attorney, Agent, or Firm* — WOMBLE BOND DICKINSON (US) LLP

(57) ABSTRACT

An aerosol delivery device is provided that includes at least one housing, a nozzle, a piezoelectric or piezomagnetic material, a control component, and a transport element. The at least one housing may enclose a reservoir configured to retain an aerosol precursor composition. The nozzle may be coupled to the housing to discharge aerosol precursor composition from the reservoir. The control component may include a microprocessor coupled to and configured to drive the piezoelectric or piezomagnetic material to vibrate and cause a discharge of components of the aerosol precursor composition and thereby produce an aerosol for inhalation by a user. And the transport element may be configured to control an amount of aerosol precursor composition delivered from the reservoir.

13 Claims, 3 Drawing Sheets

Related U.S. Application Data continuation of application No. 16/433,833, filed on Jun. 6, 2019, now Pat. No. 10,548,349, which is a continuation of application No. 15/651,548, filed on Jul. 17, 2017, now Pat. No. 10,349,674.

(51) Int. Cl.

| | | |
|---|---|---|
| *A24B 15/167* | (2020.01) | |
| *B05B 17/00* | (2006.01) | |
| *B05B 17/06* | (2006.01) | |
| *A61M 15/00* | (2006.01) | |
| *A61M 15/06* | (2006.01) | |
| *A24F 40/50* | (2020.01) | |
| *A24F 40/40* | (2020.01) | |
| *A24F 40/05* | (2020.01) | |
| *A24F 40/48* | (2020.01) | |
| *A24F 40/10* | (2020.01) | |

(52) U.S. Cl.
CPC ............ *A24F 40/40* (2020.01); *A24F 40/48* (2020.01); *A24F 40/50* (2020.01); *A61M 15/0085* (2013.01); *A61M 15/06* (2013.01); *B05B 17/0646* (2013.01); *B05B 17/0669* (2013.01); *B05B 17/0676* (2013.01); *A24F 40/10* (2020.01); *A61M 2205/276* (2013.01); *A61M 2205/3368* (2013.01); *A61M 2205/8206* (2013.01); *A61M 2205/8237* (2013.01)

(58) Field of Classification Search
USPC .................................................. 131/328–329
See application file for complete search history.

(56) References Cited

U.S. PATENT DOCUMENTS

| | | |
|---|---|---|
| 2,057,353 A | 10/1936 | Whittemore, Jr. |
| 2,104,266 A | 1/1938 | McCormick |
| 3,200,819 A | 8/1965 | Gilbert |
| 3,479,561 A | 11/1969 | Janning |
| 4,284,089 A | 8/1981 | Ray |
| 4,303,083 A | 12/1981 | Burruss, Jr. |
| 4,639,368 A | 1/1987 | Niazi et al. |
| 4,735,217 A | 4/1988 | Gerth et al. |
| 4,848,374 A | 7/1989 | Chard et al. |
| 4,907,606 A | 3/1990 | Lilja et al. |
| 4,922,901 A | 5/1990 | Brooks et al. |
| 4,945,931 A | 8/1990 | Gori |
| 4,947,874 A | 8/1990 | Brooks et al. |
| 4,947,875 A | 8/1990 | Brooks et al. |
| 4,986,286 A | 1/1991 | Roberts et al. |
| 5,019,122 A | 5/1991 | Clearman et al. |
| 5,042,510 A | 8/1991 | Curtiss et al. |
| 5,060,671 A | 10/1991 | Counts et al. |
| 5,093,894 A | 3/1992 | Deevi et al. |
| 5,144,962 A | 9/1992 | Counts et al. |
| 5,154,192 A | 10/1992 | Sprinkel et al. |
| 5,178,878 A | 1/1993 | Wehling |
| 5,223,326 A | 6/1993 | Bach |
| 5,249,586 A | 10/1993 | Morgan et al. |
| 5,261,424 A | 11/1993 | Sprinkel, Jr. |
| 5,322,075 A | 6/1994 | Deevi et al. |
| 5,353,813 A | 10/1994 | Deevi et al. |
| 5,369,723 A | 11/1994 | Counts et al. |
| 5,372,148 A | 12/1994 | McCafferty |
| 5,388,574 A | 2/1995 | Ingebrethsen et al. |
| 5,388,594 A | 2/1995 | Counts et al. |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,518,179 A | 5/1996 | Humberstone et al. |
| 5,530,225 A | 6/1996 | Hajaligol |
| 5,564,442 A | 10/1996 | MacDonald et al. |
| 5,649,554 A | 7/1997 | Sprinkel et al. |
| 5,666,977 A | 9/1997 | Higgins et al. |
| 5,687,746 A | 11/1997 | Rose et al. |
| 5,726,421 A | 3/1998 | Fleischhauer et al. |
| 5,727,571 A | 3/1998 | Meiring et al. |
| 5,743,251 A | 4/1998 | Howell et al. |
| 5,799,663 A | 9/1998 | Gross et al. |
| 5,819,756 A | 10/1998 | Mielordt |
| 5,865,185 A | 2/1999 | Collins |
| 5,865,186 A | 2/1999 | Volsey, II |
| 5,878,752 A | 3/1999 | Adams et al. |
| 5,894,841 A | 4/1999 | Voges |
| 5,934,289 A | 8/1999 | Watkins et al. |
| 5,954,979 A | 9/1999 | Counts et al. |
| 5,967,148 A | 10/1999 | Harris et al. |
| 5,996,903 A | 12/1999 | Asai et al. |
| 6,040,560 A | 3/2000 | Fleischhauer et al. |
| 6,053,176 A | 4/2000 | Adams |
| 6,089,857 A | 7/2000 | Matsuura et al. |
| 6,095,153 A | 8/2000 | Kessler et al. |
| 6,125,853 A | 10/2000 | Susa et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,296,196 B1 * | 10/2001 | Denen .................. A01M 1/205 239/102.1 |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,772,756 B2 | 8/2004 | Shayan |
| 6,803,545 B2 | 10/2004 | Blake et al. |
| 6,854,461 B2 | 2/2005 | Nichols |
| 6,854,470 B1 | 2/2005 | Pu |
| 6,974,590 B2 | 12/2005 | Pather |
| 7,040,314 B2 | 5/2006 | Nguyen et al. |
| 7,117,867 B2 | 10/2006 | Cox et al. |
| 7,217,320 B2 | 5/2007 | Kim et al. |
| 7,293,565 B2 | 11/2007 | Griffin et al. |
| 7,381,667 B2 | 6/2008 | Bergquist et al. |
| 7,513,253 B2 | 4/2009 | Kobayashi et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,079,371 B2 | 12/2011 | Robinson et al. |
| 8,127,772 B2 | 3/2012 | Montaser |
| 8,205,622 B2 | 6/2012 | Pan |
| 8,314,591 B2 | 11/2012 | Terry et al. |
| 8,365,742 B2 | 2/2013 | Hon |
| 8,402,976 B2 | 3/2013 | Fernando et al. |
| 8,424,541 B2 | 4/2013 | Crawford et al. |
| 8,499,766 B1 | 8/2013 | Newton |
| 8,528,569 B1 | 9/2013 | Newton |
| 8,539,959 B1 | 9/2013 | Scatterday |
| 8,550,069 B2 | 10/2013 | Alelov |
| 8,627,828 B2 | 1/2014 | Strickland et al. |
| 8,689,804 B2 | 4/2014 | Fernando et al. |
| 8,851,081 B2 | 10/2014 | Fernando et al. |
| 8,881,737 B2 | 11/2014 | Collett et al. |
| 8,910,640 B2 | 12/2014 | Sears et al. |
| 8,998,483 B2 | 4/2015 | Friend et al. |
| 9,220,302 B2 | 12/2015 | DePiano et al. |
| 9,254,002 B2 | 2/2016 | Chong et al. |
| 9,307,787 B2 | 4/2016 | Sun et al. |
| 9,423,152 B2 | 8/2016 | Ampolini et al. |
| 9,427,022 B2 | 8/2016 | Levin et al. |
| 9,439,454 B2 | 9/2016 | Fernando et al. |
| 9,451,791 B2 | 9/2016 | Sears et al. |
| 9,484,155 B2 | 11/2016 | Peckerar et al. |
| 9,717,279 B2 | 8/2017 | Hon |
| 9,770,055 B2 | 9/2017 | Cameron et al. |
| 9,848,648 B2 | 12/2017 | Memari et al. |
| 9,867,398 B2 | 1/2018 | Guo et al. |
| 9,936,737 B2 | 4/2018 | Cameron et al. |
| 10,004,259 B2 | 6/2018 | Sebastian et al. |
| 2002/0146242 A1 | 10/2002 | Vieira |
| 2003/0226837 A1 | 12/2003 | Blake et al. |

(56) References Cited

U.S. PATENT DOCUMENTS

| | | |
|---|---|---|
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2006/0016453 A1 | 1/2006 | Kim |
| 2006/0196518 A1 | 9/2006 | Hon |
| 2007/0044792 A1 | 3/2007 | Ivri |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2008/0084134 A1 | 4/2008 | Morita et al. |
| 2008/0085103 A1 | 4/2008 | Beland et al. |
| 2008/0092912 A1 | 4/2008 | Robinson et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0095311 A1 | 4/2009 | Hon |
| 2009/0095312 A1 | 4/2009 | Heibrich et al. |
| 2009/0126745 A1 | 5/2009 | Hon |
| 2009/0151717 A1 | 6/2009 | Bowen et al. |
| 2009/0188490 A1 | 7/2009 | Hon |
| 2009/0230117 A1 | 9/2009 | Fernando et al. |
| 2009/0242663 A1 | 10/2009 | Yu |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0018539 A1 | 1/2010 | Brinkley et al. |
| 2010/0043809 A1 | 2/2010 | Magnon |
| 2010/0083959 A1 | 4/2010 | Siller |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0309157 A1 | 12/2011 | Yang et al. |
| 2012/0042885 A1 | 2/2012 | Stone et al. |
| 2012/0055494 A1 | 3/2012 | Hunt et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0008457 A1 | 1/2013 | Zheng et al. |
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0243410 A1 | 5/2013 | Nichols |
| 2013/0180553 A1 | 7/2013 | Gaus et al. |
| 2013/0192619 A1 | 8/2013 | Tucker et al. |
| 2013/0192623 A1 | 8/2013 | Tucker et al. |
| 2013/0213419 A1 | 8/2013 | Tucker et al. |
| 2013/0255702 A1 | 10/2013 | Griffith, Jr. et al. |
| 2013/0306084 A1 | 11/2013 | Flick |
| 2013/0319404 A1 | 12/2013 | Feriani et al. |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0014125 A1 | 1/2014 | Fernando et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0157583 A1 | 6/2014 | Ward et al. |
| 2014/0209105 A1 | 7/2014 | Sears et al. |
| 2014/0238423 A1 | 8/2014 | Tucker et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0283855 A1 | 9/2014 | Hawes et al. |
| 2014/0345631 A1 | 11/2014 | Bowen et al. |
| 2015/0007838 A1 | 1/2015 | Fernando et al. |
| 2015/0020823 A1 | 1/2015 | Lipowicz et al. |
| 2015/0020830 A1 | 1/2015 | Koller |
| 2015/0034103 A1 | 2/2015 | Hon |
| 2015/0053217 A1 | 2/2015 | Steingmber et al. |
| 2015/0055494 A1 | 2/2015 | Zhou et al. |
| 2015/0059780 A1 | 3/2015 | Davis et al. |
| 2015/0101606 A1 | 4/2015 | White |
| 2015/0117841 A1 | 4/2015 | Brammer et al. |
| 2015/0128974 A1 | 5/2015 | Hon |
| 2015/0216232 A1 | 8/2015 | Bless et al. |
| 2015/0238423 A1 | 8/2015 | Wertz et al. |
| 2015/0245669 A1 | 9/2015 | Cadieux et al. |
| 2015/0257445 A1 | 9/2015 | Henry, Jr. et al. |
| 2016/0007651 A1 | 1/2016 | Ampolini et al. |
| 2016/0037826 A1 | 2/2016 | Hearn et al. |
| 2016/0066619 A1 | 3/2016 | Di Carlo |
| 2016/0213866 A1 | 7/2016 | Tan |
| 2016/0219933 A1 | 8/2016 | Henry, Jr. et al. |
| 2016/0261020 A1 | 9/2016 | Marion et al. |
| 2016/0271347 A1 | 9/2016 | Raichman |
| 2016/0325055 A1 | 11/2016 | Cameron |
| 2016/0338407 A1 | 11/2016 | Kerdemelidis |
| 2016/0345621 A1 | 12/2016 | Li et al. |
| 2016/0366946 A1 | 12/2016 | Murison et al. |
| 2017/0042241 A1 | 2/2017 | Murison et al. |
| 2017/0064997 A1 | 3/2017 | Murison et al. |
| 2017/0119059 A1 | 5/2017 | Zuber et al. |
| 2017/0157341 A1 | 6/2017 | Pandya et al. |
| 2017/0238608 A1 | 8/2017 | Matsumoto et al. |
| 2017/0303594 A1 | 10/2017 | Cameron et al. |
| 2017/0367273 A1* | 12/2017 | Bylsma ............... G02B 6/001 |
| 2017/0368273 A1 | 12/2017 | Rubin |
| 2018/0038838 A1 | 2/2018 | Karancsi et al. |
| 2018/0090923 A1 | 3/2018 | Li et al. |
| 2018/0153217 A1 | 6/2018 | Liu et al. |
| 2018/0161525 A1 | 6/2018 | Liu et al. |
| 2018/0169691 A1 | 6/2018 | Macloughlin et al. |
| 2018/0289076 A1 | 10/2018 | Manca et al. |
| 2019/0014819 A1 | 1/2019 | Sur |
| 2019/0281890 A1 | 9/2019 | Sur |

FOREIGN PATENT DOCUMENTS

| | | |
|---|---|---|
| CA | 2 641 869 | 5/2010 |
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 101618245 A | 1/2010 |
| CN | 201379072 | 1/2010 |
| CN | 105962424 A | 9/2016 |
| CN | 106714974 A | 5/2017 |
| CN | 206423575 | 8/2017 |
| DE | 10 2006 004 484 | 8/2007 |
| DE | 102006041042 | 3/2008 |
| DE | 20 2009 010 400 | 11/2009 |
| EA | 023124 B1 | 4/2016 |
| EP | 0 295 122 | 12/1988 |
| EP | 0 430 566 | 6/1991 |
| EP | 0 845 220 | 6/1998 |

(56) References Cited

FOREIGN PATENT DOCUMENTS

| | | |
|---|---|---|
| EP | 1 618 803 | 1/2006 |
| EP | 1618803 A1 | 1/2006 |
| EP | 2 316 286 | 5/2011 |
| EP | 3 228 345 | 10/2017 |
| EP | 3 272 237 | 1/2018 |
| EP | 3 278 678 | 2/2018 |
| EP | 3 287 019 | 2/2018 |
| EP | 3 298 912 | 3/2018 |
| EP | 3 305 104 | 4/2018 |
| GB | 2469850 | 11/2010 |
| JP | 2006-524494 A | 11/2006 |
| JP | 2013-102764 A | 5/2013 |
| RU | 2 600 092 C2 | 10/2016 |
| WO | 9706786 A1 | 2/1997 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | 2012026963 A2 | 3/2012 |
| WO | WO 2012/026963 | 3/2012 |
| WO | 2012062600 A1 | 5/2012 |
| WO | WO 2012/062600 | 5/2012 |
| WO | WO 2012/072762 | 6/2012 |
| WO | WO 2012/100523 | 8/2012 |
| WO | WO 2013/089551 | 6/2013 |
| WO | 2014182736 A1 | 11/2014 |
| WO | 2015/077645 A1 | 5/2015 |
| WO | WO 2015/168588 | 5/2015 |
| WO | 2016/075749 A1 | 5/2016 |
| WO | WO 2016/165055 | 10/2016 |
| WO | WO 2017/051181 | 3/2017 |
| WO | WO 2017/063256 | 4/2017 |
| WO | WO 2017/149165 | 9/2017 |
| WO | WO 2017/175218 | 10/2017 |
| WO | WO 2017/201710 | 11/2017 |
| WO | WO 2017/201716 | 11/2017 |
| WO | WO 2017/202014 | 11/2017 |
| WO | WO 2017/206022 | 12/2017 |
| WO | WO 2017/206480 | 12/2017 |
| WO | WO 2017/215221 | 12/2017 |
| WO | WO 2018/000756 | 1/2018 |
| WO | WO 2018/000760 | 1/2018 |
| WO | WO 2018/000761 | 1/2018 |
| WO | WO 2018/000829 | 1/2018 |
| WO | WO 2018/001105 | 1/2018 |
| WO | WO 2018/001106 | 1/2018 |
| WO | WO 2018/023890 | 2/2018 |
| WO | WO 2018/040380 | 3/2018 |
| WO | WO 2018/058884 | 4/2018 |
| WO | WO 2018/058883 | 5/2018 |
| WO | WO 2018095312 | 5/2018 |
| WO | WO 2018/053955 | 3/2019 |

OTHER PUBLICATIONS

Yeo et al., "Ultrafast microfluidics using surface acoustic waves", American Institute of Physics, 2009, pp. 1-23.
Qi et al., "Miniature inhalation therapy platform using surface acoustic wave microfluidic atomization", The Royal Society of Chemistry, May 2009, pp. 2184-2193.
Ariyakul et al., "Olfactory Display Using a Miniaturized Pump and a SAW Atomizer for Presenting Low-volatile Scents", IEEE Virtual Reality, 2011, pp. 193-194.
Olszewski et al., "A silicon-based MEMS vibrating mesh nebulizer for inhaled drug delivery", Procedia Engineering, 2016, pp. 1521-1524.
Hawkins et al., "Vibrating Mesh Nebulizer Reference Design", Microchip Technology Inc., 2016- 2017, pp. 1-50.
Piezoelectric Micro Pump—Takasago Fluidic System, http://www.takasago-fluidics.com/products/products_pump/ transfer/, pp. 1-3, Retrieved from Internet May 24, 2017.
Pump up the pressure thinXXS launches a further micro pump model, http://www.thinxxs.com/index.php?id=70&L=1&type=98, pp. 1-2, Retrieved from Internet May 24, 2017.
Bong-Kee Lee et al., "Replication Quality of Flow-Through Microfilters in Microfluidic Lab-on-a-Chip for Blood Typing by Microinjection Molding", pp. 1-8, vol. 130, Apr. 2008.
Small for Big Things, nanobioSensors & MicroActuators Learning Lab, University of Buffalo the State University of New York, EE 428/528 BioMEMS & Lab-on-a-chip, Professor Kwang W. Oh, Lecture 09: Microfluids, PowerPoint 1-17.
Bartels Micropumps, http:www.bartels-mikrotechnik.de/index.php/en/products/micropumps, pp. 1-3, Retrieved from Internet May 22, 2017.
Andrew Michalow, Sensors Online, "Postage-Stamp-Sized Micropumps for Both Gas and Liquid Sensor Systems", pp. 1-8, Jul. 1, 2011.
Microchip, "Go Smaller with Your Drug Delivery Devices", Nebulizer, pp. 1-3, http://www.microchip.com/designs- center/medical/applications/nebulizers, Retrieved from Internet May 16, 2017.
MEMS Products, http://www.microfab.de/printable/mems/index.html, p. 1, Retrieved from Internet May 16, 2017.
Microchip, "Vibrating Mesh Nebulizer Demonstration Board", Microchip Technology Inc., pp. 1-3, http://www.microchip.com/promo/vibrating-mesh-nebulizer-demo, Retrieved from Internet May 16, 2017.
Microchip, "Vibrating Mesh Nebulizer Reference Design", AN2265, Microchip Technology Inc., pp. 1-50, Created Jan. 16, 2017.
International Search Report from International Appl. No. PCT/IB2018,055259, dated Nov. 29, 2018.
Niu Wangje et al. "Electronic Technology: Multivibrator with adjustable duty cycle", 11.3.3, Gong Qiang, Xidian University Press, p. 294. 6 pages.
Zhu, D. et al. Electronic Cigarettes. Yuman University Press, Aug. 31, 2015. 8 pages.
Weng, F. Observation Method Smoking Cessation Manual. Jinan University Press, Aug. 31, 2015. 21 pages.

* cited by examiner

NO-HEAT, NO-BURN SMOKING ARTICLE

CROSS-REFERENCE TO RELATED APPLICATIONS

This application is a continuation of U.S. patent application Ser. No. 16/719,178, filed on Dec. 18, 2019, which is a continuation of U.S. patent application Ser. No. 16/433,833, filed on Jun. 6, 2019, which is a continuation of U.S. patent application Ser. No. 15/651,548, filed on Jul. 17, 2017, each of which is incorporated herein in its entirety by reference.

TECHNOLOGICAL FIELD

The present disclosure relates to aerosol delivery devices such as smoking articles that produce aerosol. The smoking articles may be configured to dispense an aerosol precursor, which may incorporate materials that may be made or derived from, or otherwise incorporate tobacco, the precursor being capable of forming an inhalable substance for human consumption.

BACKGROUND

Many devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous alternative smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 8,881,737 to Collett et al., U.S. Pat. App. Pub. No. 2013/0255702 to Griffith Jr. et al., U.S. Pat. App. Pub. No. 2014/0000638 to Sebastian et al., U.S. Pat. App. Pub. No. 2014/0096781 to Sears et al., U.S. Pat. App. Pub. No. 2014/0096782 to Ampolini et al., U.S. Pat. App. Pub. No. 2015/0059780 to Davis et al., and U.S. patent application Ser. No. 15/222,615 to Watson et al., filed Jul. 28, 2016, all of which are incorporated herein by reference. See also, for example, the various implementations of products and heating configurations described in the background sections of U.S. Pat. No. 5,388,594 to Counts et al. and U.S. Pat. No. 8,079,371 to Robinson et al., which are incorporated by reference. Additional examples of smoking articles are described in U.S. Pat. No. 5,388,574 to Ingebrethsen, EP Pat. Pub. No. 1,618,803 to Hon, PCT Pat. App. Pub. No. WO 2012/062600 to Andersson et al., and U.S. Pat. App. Pub. No. 2015/0128974 to Hon, all of which are incorporated herein by reference.

However, it may be desirable to provide aerosol delivery devices with improved electronics such as may extend usability of the devices.

BRIEF SUMMARY

The present disclosure relates to aerosol delivery devices, methods of forming such devices, and elements of such devices. The present disclosure includes, without limitation, the following example implementations.

Some example implementations provide an aerosol delivery device comprising at least one housing enclosing a reservoir configured to retain an aerosol precursor composition; a nozzle coupled to the housing to discharge aerosol precursor composition from the reservoir, the nozzle including a piezoelectric or piezomagnetic material surrounding a mesh; and a control component including a microprocessor coupled to and configured to drive the piezoelectric or piezomagnetic material to vibrate and cause a discharge of components of the aerosol precursor composition through the mesh and thereby produce an aerosol for inhalation by a user, the components of the aerosol precursor composition discharged through the mesh having a diameter of less than one micrometer.

In some example implementations of the aerosol delivery device of the preceding or any subsequent example implementation, or any combination thereof, the piezoelectric or piezomagnetic material has a resonant frequency of up to 400 megahertz.

In some example implementations of the aerosol delivery device of the preceding or any subsequent example implementation, or any combination thereof, the piezoelectric or piezomagnetic material has a resonant frequency of 1,000 kilohertz, and the mesh is a microelectromechanical systems (MEMS) device.

In some example implementations of the aerosol delivery device of any preceding or any subsequent example implementation, or any combination thereof, the piezoelectric or piezomagnetic material has a resonant frequency of 130 kilohertz, and the mesh is a stainless steel mesh.

In some example implementations of the aerosol delivery device of any preceding or any subsequent example implementation, or any combination thereof, the mesh has a curved surface.

In some example implementations of the aerosol delivery device of any preceding or any subsequent example implementation, or any combination thereof, the aerosol delivery device further comprises a power source configured to generate a voltage output, the power source being a rechargeable battery having a nominal voltage between 3.7 and 4.1 volts, wherein the control component further includes a boost regulator between the power source and an electrical load that includes the piezoelectric or piezomagnetic material, the boost regulator being configured to step up the voltage output of the power source to a higher voltage, and wherein the microprocessor being configured to drive the piezoelectric or piezomagnetic material includes being configured to drive the boost regulator to output the higher voltage to power the piezoelectric or piezomagnetic material to vibrate.

In some example implementations of the aerosol delivery device of any preceding or any subsequent example implementation, or any combination thereof, the control component further includes an electronic oscillator coupled to and between the microprocessor and piezoelectric or piezomagnetic material, and wherein the microprocessor being configured to drive the piezoelectric or piezomagnetic material includes being configured to drive the electronic oscillator to produce a periodic, oscillating electronic signal to drive the piezoelectric or piezomagnetic material at a resonant frequency thereof.

In some example implementations of the aerosol delivery device of any preceding or any subsequent example implementation, or any combination thereof, the microprocessor is configured to output a pulsing signal to drive the electronic oscillator to produce the periodic, oscillating electronic signal, the pulsing signal having a programmable duty cycle.

In some example implementations of the aerosol delivery device of any preceding or any subsequent example implementation, or any combination thereof, the microprocessor is configured to control the electronic oscillator to produce the periodic, oscillating electronic signal having a frequency of 1,000 kilohertz that corresponds to the resonant frequency of the piezoelectric or piezomagnetic material.

In some example implementations of the aerosol delivery device of any preceding or any subsequent example implementation, or any combination thereof, the piezoelectric or piezomagnetic material is piezoelectric material, and the electronic oscillator is electrically coupled to the piezoelectric material and configured to produce the periodic, oscillating electronic signal to drive the piezoelectric material to vibrate.

In some example implementations of the aerosol delivery device of any preceding or any subsequent example implementation, or any combination thereof, the piezoelectric or piezomagnetic material is piezomagnetic material, and the control component further includes a pair of magnets on either side of the piezomagnetic material; and a phase splitter configured to receive the periodic, oscillating electronic signal and produce a pair of periodic, oscillating electronic signals that are antiphase, the phase splitter being configured to produce the pair of periodic, oscillating electronic signals to drive the pair of magnets to produce periodic, oscillating magnetic fields that are antiphase and thereby drive the piezomagnetic material to vibrate. In some example implementations of the aerosol delivery device of any preceding or any subsequent example implementation, or any combination thereof, the control component further includes a boost regulator between a power source and an electrical load that includes the piezoelectric or piezomagnetic material, the boost regulator being configured to step up a voltage output of the power source to a higher voltage; and an electronic oscillator coupled to and between the boost regulator and piezoelectric or piezomagnetic material, wherein the microprocessor being configured to drive the piezoelectric or piezomagnetic material includes being configured to drive the boost regulator to output the higher voltage to power the electronic oscillator to produce a periodic, oscillating electronic signal to drive the piezoelectric or piezomagnetic material to vibrate at a resonant frequency thereof.

In some example implementations of the aerosol delivery device of any preceding or any subsequent example implementation, or any combination thereof, the microprocessor is configured to output a pulsing signal to drive the boost regular and thereby the electronic oscillator to produce the periodic, oscillating electronic signal, the pulsing signal having a programmable duty cycle.

In some example implementations of the aerosol delivery device of any preceding or any subsequent example implementation, or any combination thereof, the microprocessor is configured to control the electronic oscillator to produce the periodic, oscillating electronic signal having a frequency of 1,000 kilohertz that corresponds to the resonant frequency of the piezoelectric or piezomagnetic material.

In some example implementations of the aerosol delivery device of any preceding or any subsequent example implementation, or any combination thereof, the piezoelectric or piezomagnetic material is piezomagnetic material, and the control component further includes a pair of magnets on either side of the piezomagnetic material; and a phase splitter configured to receive the periodic, oscillating electronic signal and produce a pair of periodic, oscillating electronic signals that are antiphase, the phase splitter being configured to produce the pair of periodic, oscillating electronic signals to drive the pair of magnets to produce periodic, oscillating magnetic fields that are antiphase and thereby drive the piezomagnetic material to vibrate.

In some example implementations of the aerosol delivery device of any preceding or any subsequent example implementation, or any combination thereof, the aerosol delivery device further comprises the power source configured to generate the voltage output, the power source being a rechargeable battery having a nominal voltage between 3.7 and 4.1 volts.

In some example implementations of the aerosol delivery device of any preceding or any subsequent example implementation, or any combination thereof, the aerosol delivery device further comprises a current sensor configured to measure electric current through the piezoelectric or piezomagnetic material, wherein the microprocessor is configured to control operation of at least one functional element of the aerosol delivery device in response to the electric current so measured.

In some example implementations of the aerosol delivery device of any preceding or any subsequent example implementation, or any combination thereof, the aerosol delivery device further comprises a micro pump proximate a reservoir side of the mesh to deliver aerosol precursor composition from the reservoir to the mesh for discharge of components thereof.

In some example implementations of the aerosol delivery device of any preceding or any subsequent example implementation, or any combination thereof, aerosol precursor composition is delivered from the reservoir to the mesh for discharge of components thereof, and wherein the aerosol delivery device further comprises a micro filter proximate a reservoir side of the mesh to filter the aerosol precursor composition delivered from the reservoir to the mesh for discharge of components thereof.

In some example implementations of the aerosol delivery device of any preceding or any subsequent example implementation, or any combination thereof, the aerosol delivery device further comprises a micro pump proximate a reservoir side of the mesh to deliver aerosol precursor composition from the reservoir to the mesh for discharge of components thereof; and a micro filter between the micro pump and the mesh to filter the aerosol precursor composition delivered from the reservoir to the mesh.

In some example implementations of the aerosol delivery device of any preceding or any subsequent example implementation, or any combination thereof, the aerosol precursor composition comprises glycerin and nicotine.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE DRAWING(S)

Having thus described the disclosure in the foregoing general terms, reference will now be made to the accompanying drawings, which are not necessarily drawn to scale, and wherein:

DETAILED DESCRIPTION

Figure 1:
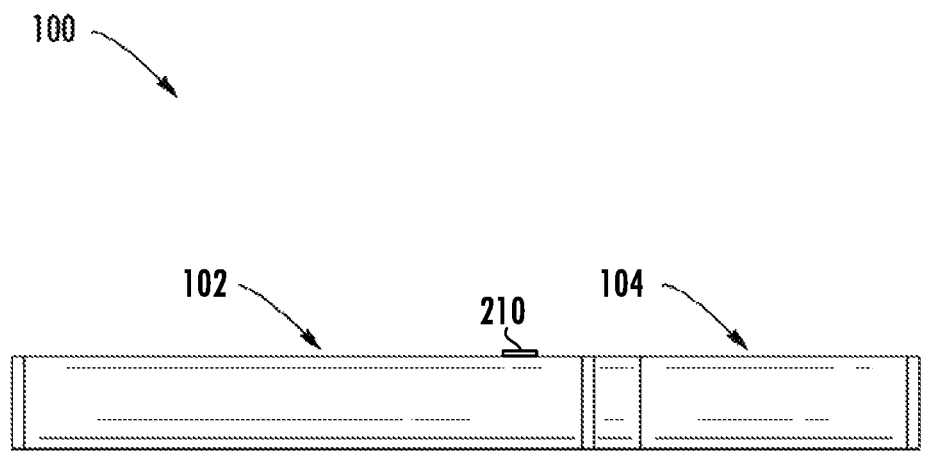
FIG. 1 illustrates a side view of an aerosol delivery device including a cartridge coupled to a control body, according to an example implementation of the present disclosure.

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise. Also, while reference may be made herein to quantitative measures, values, geometric relationships or the like, unless otherwise stated, any one or more if not all of these may be absolute or approximate to account for acceptable variations that may occur, such as those due to engineering tolerances or the like.

As described hereinafter, example implementations of the present disclosure relate to aerosol delivery devices. Aerosol delivery devices according to the present disclosure use electrical energy to dispense a material (preferably without combusting the material to any significant degree) in the form of an inhalable substance; and components of such systems have the form of articles most preferably are sufficiently compact to be considered hand-held devices. That is, use of components of preferred aerosol delivery devices does not result in the production of smoke in the sense that aerosol results principally from by-products of combustion or pyrolysis of tobacco, but rather, use of those preferred systems results in the production of an aerosol resulting from passage of certain components incorporated therein through a vibrating piezoelectric or piezomagnetic mesh. In some example implementations, components of aerosol delivery devices may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

While the systems are generally described herein in terms of implementations associated with aerosol delivery devices such as so-called "e-cigarettes," it should be understood that the mechanisms, components, features, and methods may be embodied in many different forms and associated with a variety of articles. For example, the description provided herein may be employed in conjunction with implementations of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of implementations relating to aerosol delivery devices by way of example only, and may be embodied and used in various other products and methods.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of an aerosol (i.e., a suspension of fine solid particles or liquid droplets in a gas). Alternatively, inhalable substances can be in the form of a vapor (i.e., a substance that is in the gas phase at a temperature lower than its critical point). For purposes of simplicity, the term "aerosol" as used herein is meant to include aerosols, vapors and gases of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Aerosol delivery devices of the present disclosure generally include a number of components provided within an outer body or shell, which may be referred to as a housing. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary housing or the elongated housing can be formed of two or more separable bodies. For example, an aerosol delivery device can comprise an elongated shell or body that can be substantially tubular in shape and, as such, resemble the shape of a conventional cigarette or cigar. In one example, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., an accumulator such as a rechargeable battery and/or rechargeable supercapacitor, and various electronics for controlling the operation of that article), and at the other end and removably coupleable thereto, an outer body or shell containing a disposable portion (e.g., a disposable flavor-containing cartridge). More specific formats, configurations and arrangements of components within the single housing type of unit or within a multi-piece separable housing type of unit will be evident in light of the further disclosure provided herein. Additionally, various aerosol delivery device designs and component arrangements can be appreciated upon consideration of the commercially-available electronic aerosol delivery devices.

Aerosol delivery devices of the present disclosure most preferably comprise some combination of a power source (i.e., an electrical power source), at least one control component (e.g., means for actuating, controlling, regulating and ceasing power for aerosol disbursement, such as by controlling electrical current flow the power source to other components of the article—e.g., a microprocessor, individually or as part of a microcontroller), a vibratable piezoelectric or piezomagnetic mesh, which alone or in combination with one or more further elements may be commonly referred to as an "atomizer", an aerosol precursor composition (e.g., commonly a liquid capable of yielding an aerosol upon disbursement through a vibrating piezoelectric or piezomagnetic mesh, such as ingredients commonly referred to as "smoke juice," "e-liquid" and "e-juice"), and a mouthend region or tip for allowing draw upon the aerosol delivery device for aerosol inhalation (e.g., a defined airflow path through the article such that aerosol generated can be withdrawn therefrom upon draw).

Alignment of the components within the aerosol delivery device of the present disclosure can vary. In specific implementations, the aerosol precursor composition can be located near an end of the aerosol delivery device which may be configured to be positioned proximal to the mouth of a user so as to maximize aerosol delivery to the user. Other configurations, however, are not excluded. Generally, the piezoelectric/piezomagnetic mesh can be positioned sufficiently near the aerosol precursor composition so that when the mesh is vibrating, the aerosol precursor (as well as one or more flavorants, medicaments, or the like that may likewise be provided for delivery to a user) is drawn through the mesh and forms an aerosol for delivery to the user. When the aerosol precursor composition is dispensed through the mesh, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of an aerosol or vapor or mixture thereof, wherein such terms are also interchangeably used herein except where otherwise specified.

As noted above, the aerosol delivery device may incorporate a battery or other electrical power source to provide current flow sufficient to provide various functionalities to the aerosol delivery device, such as powering of a piezoelectric/piezomagnetic mesh, powering of control systems, powering of indicators, and the like. The power source can take on various implementations. Preferably, the power source is able to deliver sufficient power to cause the piezoelectric/piezomagnetic mesh to rapidly vibrate to provide for aerosol formation and power the aerosol delivery device through use for a desired duration of time. The power source preferably is sized to fit conveniently within the aerosol delivery device so that the aerosol delivery device can be easily handled. Additionally, a preferred power source is of a sufficiently light weight to not detract from a desirable smoking experience.

More specific formats, configurations and arrangements of components within the aerosol delivery devices of the present disclosure will be evident in light of the further disclosure provided hereinafter. Additionally, the selection and arrangement of various aerosol delivery device components can be appreciated upon consideration of commercially-available electronic aerosol delivery devices. Further information regarding formats, configurations and arrangements of components within the aerosol delivery devices of the present disclosure, as well as commercially-available electronic aerosol delivery devices, may be found in PCT Pat. App. Pub. No. WO 2015/168588 to Ademe et al., and U.S. patent application Ser. No. 15/291,771 to Sur et al., filed Oct. 12, 2016, which are incorporated herein by reference.

FIG. 1 illustrates a side view of an aerosol delivery device 100 including a control body 102 and a cartridge 104, according to various example implementations of the present disclosure. In particular, FIG. 1 illustrates the control body and the cartridge coupled to one another. The control body and the cartridge may be detachably aligned in a functioning relationship. Various mechanisms may connect the cartridge to the control body to result in a threaded engagement, a press-fit engagement, an interference fit, a magnetic engagement or the like. The aerosol delivery device may be substantially rod-like, substantially tubular shaped, or substantially cylindrically shaped in some example implementations when the cartridge and the control body are in an assembled configuration. The aerosol delivery device may also be substantially rectangular, rhomboidal or triangular in cross-section, multifaceted shapes, or the like, some of which may lend itself to greater compatibility with a substantially flat or thin-film power source, such as a power source including a flat battery.

The control body 102 and cartridge 104 may include separate, respective housings or outer bodies, which may be formed of any of a number of different materials. The housing may be formed of any suitable, structurally-sound material. In some examples, the housing may be formed of a metal or alloy, such as stainless steel, aluminum or the like. Other suitable materials include various plastics (e.g., polycarbonate), metal-plating over plastic, ceramics and the like.

In some example implementations, one or both of the control body 102 or the cartridge 104 of the aerosol delivery device 100 may be referred to as being disposable or as being reusable. For example, the control body may have a replaceable battery, rechargeable battery (e.g., rechargeable thin-film solid state battery) or rechargeable supercapacitor, and thus may be combined with any type of recharging technology, including connection to a typical wall outlet, connection to a car charger (i.e., a cigarette lighter receptacle), connection to a computer, such as through a universal serial bus (USB) cable or connector, connection to a photovoltaic cell (sometimes referred to as a solar cell) or solar panel of solar cells, wireless connection to a Radio Frequency (RF), wireless connection to induction-based charging pads, or connection to a RF-to-DC converter.

Figure 2:
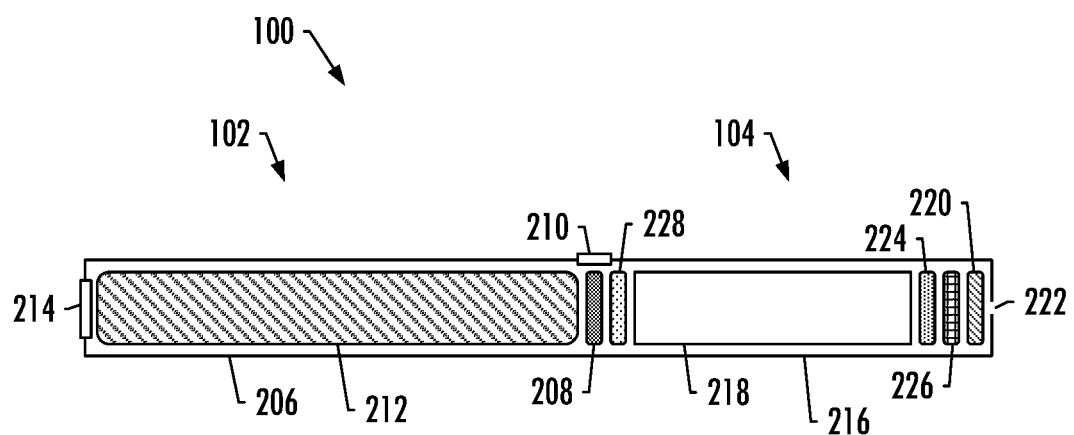
FIG. 2 is a partially cut-away view of the aerosol delivery device according to various example implementations.

FIG. 2 more particularly illustrates the aerosol delivery device 100, in accordance with some example implementations. As seen in the cut-away view illustrated therein, again, the aerosol delivery device can comprise a control body 102 and a cartridge 104 each of which include a number of respective components. The components illustrated in FIG. 2 are representative of the components that may be present in a control body and cartridge and are not intended to limit the scope of components that are encompassed by the present disclosure. As shown, for example, the control body can be formed of a control body shell 206 that can include a control component 208 (e.g., a microprocessor, individually or as part of a microcontroller), an input device 210, a power source 212 and one or more light-emitting diodes (LEDs) 214, quantum dot enabled LEDs or the like, and such components can be variably aligned. Examples of a suitable control component include the PIC16(L)F1713/6 microcontrollers from Microchip Technology Inc., which is described in Microchip Technology, Inc., AN2265, *Vibrating Mesh Nebulizer Reference Design* (2016), which is incorporated by reference. The input device may be or include, for example, a switch that may be implemented in a number of different manners, such as a push button, or a touch switch or other touch sensitive surface. In some example implementations, the input device may include a flow sensor configured to detect a user drawing on the aerosol delivery device.

The power source 212 may include, for example, a battery (single-use or rechargeable), rechargeable supercapacitor, rechargeable solid-state battery (SSB), rechargeable lithium-ion battery (LiB) or the like, or some combination thereof. Some examples of a suitable power source are provided in U.S. patent application Ser. No. 14/918,926 to Sur et al., filed Oct. 21, 2015, which is incorporated herein by reference. Other examples of a suitable power source are provided in U.S. Pat. App. Pub. No. 2014/0283855 to Hawes et al., U.S. Pat. App. Pub. No. 2014/0014125 to Fernando et al., U.S. Pat. App. Pub. No. 2013/0243410 to Nichols et al., U.S. Pat. App. Pub. No. 2010/0313901 to Fernando et al., and U.S. Pat. App. Pub. No. 2009/0230117 to Fernando et al., all of which are incorporated herein by reference.

The LED 214 may be one example of a suitable visual indicator with which the aerosol delivery device 100 may be equipped. Other indicators such as audio indicators (e.g., speakers), haptic indicators (e.g., vibration motors) or the like can be included in addition to or as an alternative to visual indicators such as the LED, quantum dot enabled LEDs.

The cartridge 104 can be formed of a cartridge shell 216 enclosing a reservoir 218 configured to retain the aerosol precursor composition, and including a nozzle 220 having a piezoelectric/piezomagnetic mesh. In various configurations, this structure may be referred to as a tank; and accordingly, the terms "cartridge," "tank" and the like may be used interchangeably to refer to a shell or other housing enclosing a reservoir for aerosol precursor composition, and including a nozzle.

The reservoir 218 illustrated in FIG. 2 can be a container or can be a fibrous reservoir, as presently described. The reservoir may be in fluid communication with the nozzle 220 for transport of an aerosol precursor composition stored in the reservoir housing to the nozzle. An opening 222 may be present in the cartridge shell 216 (e.g., at the mouthend) to allow for egress of formed aerosol from the cartridge 104.

In some examples, a transport element may be positioned between the reservoir 218 and nozzle 220, and configured to control an amount of aerosol precursor composition passed or delivered from the reservoir to the nozzle. In some examples, a microfluidic chip may be embedded in the cartridge 104, and the amount and/or mass of aerosol precursor composition delivered from the reservoir may be controlled by one or more microfluidic components. One example of a microfluidic component is a micro pump 224, such as one based on microelectromechanical systems (MEMS) technology. Examples of suitable micro pumps include the model MDP2205 micro pump and others from thinXXS Microtechnology AG, the mp5 and mp6 model micro pumps and others from Bartels Mikrotechnik GmbH, and piezoelectric micro pumps from Takasago Fluidic Systems.

As also shown, in some examples, a micro filter 226 may be positioned between the micro pump 224 and nozzle 220 to filter aerosol precursor composition delivered to the nozzle. Like the micro pump, the micro filter is a microfluidic component. Examples of suitable micro filters include flow-through micro filters those manufactured using lab-on-a-chip (LOC) techniques.

In use, when the input device 210 detects user input to activate the aerosol delivery device, the piezoelectric/piezomagnetic mesh is activated to vibrate and thereby draw aerosol precursor composition through the mesh. This forms droplets of aerosol precursor composition that combine with air to form an aerosol. The aerosol is whisked, aspirated or otherwise drawn away from the mesh and out the opening 224 in the mouthend of the aerosol delivery device.

In some examples, the aerosol delivery device 100 may include a number of additional software-controlled functions. For example, the aerosol delivery device may include a power-source protection circuit configured to detect power-source input, loads on the power-source terminals, and charging input. The power-source protection circuit may include short-circuit protection, under-voltage lock out and/or over-voltage charge protection, battery temperature compensation. The aerosol delivery device may also include components for ambient temperature measurement, and its control component 208 may be configured to control at least one functional element to inhibit power-source charging—particularly of any battery—if the ambient temperature is below a certain temperature (e.g., 0° C.) or above a certain temperature (e.g., 45° C.) prior to start of charging or during charging.

Additionally or alternatively, in some examples, power delivery from the power source 212 may vary over the course of each puff on the aerosol delivery device 100 according to a power control mechanism. The device may include a "long puff" safety timer such that in the event that a user or component failure (e.g., input device 210) causes the aerosol delivery device to attempt to puff continuously, the control component 208 may control at least one functional element to terminate the puff automatically after some period of time (e.g., four seconds). Further, the time between puffs on the aerosol delivery device may be restricted to less than a period of time (e.g., 100 seconds). A watchdog safety timer may automatically reset the aerosol delivery device if its control component or software running on it becomes unstable and does not service the timer within an appropriate time interval (e.g., eight seconds). Further safety protection may be provided in the event of a defective or otherwise failed input device 210, such as by permanently disabling the aerosol delivery device in order to prevent inadvertent dispensing of aerosol. A puffing limit switch may deactivate the device in the event of an input device fail causing the device to continuously activate without stopping after the four second maximum puff time.

The aerosol delivery device 100 may include a puff tracking algorithm configured to lockout the nozzle 220 from dispensing aerosol once a defined number of puffs has been achieved for an attached cartridge (based on the number of available puffs calculated in light of the e-liquid charge in the cartridge). The aerosol delivery device may include a sleep, standby or low-power mode function whereby power delivery may be automatically cut off after a defined period of non-use. Further safety protection may be provided in that all charge/discharge cycles of the power source 212 may be monitored by the control component 208 over its lifetime. After the power source has attained the equivalent of a predetermined number (e.g., 200) of full discharge and full recharge cycles, it may be declared depleted, and the control component may control at least one functional element to prevent further charging of the power source.

The various components of an aerosol delivery device according to the present disclosure can be chosen from components described in the art and commercially available. Examples of batteries that can be used according to the disclosure are described in U.S. Pat. No. 9,484,155 to Peckerar et al., which is incorporated herein by reference.

The aerosol delivery device 100 can incorporate the input device 210 such as a switch, sensor or detector for control of supply of electric power to the piezoelectric/piezomagnetic mesh of the nozzle 220 when aerosol generation is desired (e.g., upon draw during use). As such, for example, there is provided a manner or method of turning off power to the mesh when the aerosol delivery device is not being drawn upon during use, and for turning on power to actuate or trigger the dispensing of aerosol from the nozzle during draw. Additional representative types of sensing or detection mechanisms, structure and configuration thereof, components thereof, and general methods of operation thereof, are described in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference.

The aerosol delivery device 100 most preferably incorporates the control component 208 or another control mechanism for controlling the amount of electric power to the piezoelectric/piezomagnetic mesh during draw. Representative types of electronic components, structure and configuration thereof, features thereof, and general methods of operation thereof, are described in U.S. Pat. No. 4,735,217 to Gerth et al., U.S. Pat. No. 4,947,874 to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. Pub. No. 8,881,737 to Collet et al., U.S. Pat. No. 9,423,152 to Ampolini et al., U.S. Pat. No. 9,439,454 to Fernando et al., and U.S. Pat. App. Pub. No. 2015/0257445 to Henry et al., all of which are incorporated herein by reference.

Representative types of substrates, reservoirs or other components for supporting the aerosol precursor are described in U.S. Pat. No. 8,528,569 to Newton, U.S. Pat. App. Pub. No. 2014/0261487 to Chapman et al., U.S. Pat. App. Pub. No. 2015/0059780 to Davis et al., and U.S. Pat. App. Pub. No. 2015/0216232 to Bless et al., all of which are incorporated herein by reference. Additionally, various wicking materials, and the configuration and operation of those wicking materials within certain types of electronic cigarettes, are set forth in U.S. Pat. No. 8,910,640 to Sears et al., which is incorporated herein by reference.

The aerosol precursor composition, also referred to as a vapor precursor composition, may comprise a variety of components including, by way of example, a polyhydric alcohol (e.g., glycerin, propylene glycol or a mixture thereof), nicotine, tobacco, tobacco extract and/or flavorants. In some examples, the aerosol precursor composition comprises glycerin and nicotine. Representative types of aerosol precursor components and formulations also are set forth and characterized in U.S. Pat. No. 7,217,320 to Robinson et al., U.S. Pat. No. 9,254,002 to Chong et al., U.S. Pat. No. 8,881,737 to Collett et al., U.S. Pat. Pub. No. 2013/0008457 to Zheng et al., U.S. Pat. Pub. No. 2015/0020823 to Lipowicz et al., and U.S. Pat. Pub. No. 2015/0020830 to Koller, as well as PCT Pat. App. Pub. No. WO 2014/182736 to Bowen et al., and U.S. patent application Ser. No. 15/222,615 to Watson et al., filed Jul. 28, 2016, the disclosures of which are incorporated herein by reference. Other aerosol precursors that may be employed include the aerosol precursors that have been incorporated in the VUSE® product by R. J. Reynolds Vapor Company, the BLU™ product by Imperial Tobacco Group PLC, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

Implementations of effervescent materials can be used with the aerosol precursor, and are described, by way of example, in U.S. Pat. App. Pub. No. 2012/0055494 to Hunt et al., which is incorporated herein by reference. Further, the use of effervescent materials is described, for example, in U.S. Pat. No. 4,639,368 to Niazi et al., U.S. Pat. No. 5,178,878 to Wehling et al., U.S. Pat. No. 5,223,264 to Wehling et al., U.S. Pat. No. 6,974,590 to Pather et al., U.S. Pat. No. 7,381,667 to Bergquist et al., U.S. Pat. No. 8,424,541 to Crawford et al., and U.S. Pat. No. 8,627,828 to Strickland et al., as well as U.S. Pat. No. 9,307,787 to Sun et al., U.S. Pat. App. Pub. No. 2010/0018539 to Brinkley et al., and PCT Pat. App. Pub. No. WO 97/06786 to Johnson et al., all of which are incorporated by reference herein. Additional description with respect to implementations of aerosol precursor compositions, including description of tobacco or components derived from tobacco included therein, is provided in U.S. patent application Ser. Nos. 15/216,582 and 15/216,590, each filed Jul. 21, 2016 and each to Davis et al., which are incorporated herein by reference.

Additional representative types of components that yield visual cues or indicators may be employed in the aerosol delivery device 100, such as visual indicators and related components, audio indicators, haptic indicators and the like. Examples of suitable LED components, and the configurations and uses thereof, are described in U.S. Pat. No. 5,154,192 to Sprinkel et al., U.S. Pat. No. 8,499,766 to Newton, U.S. Pat. No. 8,539,959 to Scatterday, and U.S. Pat. No. 9,451,791 to Sears et al., all of which are incorporated herein by reference.

Yet other features, controls or components that can be incorporated into aerosol delivery devices of the present disclosure are described in U.S. Pat. No. 5,967,148 to Harris et al., U.S. Pat. No. 5,934,289 to Watkins et al., U.S. Pat. No. 5,954,979 to Counts et al., U.S. Pat. No. 6,040,560 to Fleischhauer et al., U.S. Pat. No. 8,365,742 to Hon, U.S. Pat. No. 8,402,976 to Fernando et al., U.S. Pat. App. Pub. No. 2005/0016550 to Katase, U.S. Pat. No. 8,689,804 to Fernando et al., U.S. Pat. App. Pub. No. 2013/0192623 to Tucker et al., U.S. Pat. No. 9,427,022 to Leven et al., U.S. Pat. App. Pub. No. 2013/0180553 to Kim et al., U.S. Pat. App. Pub. No. 2014/0000638 to Sebastian et al., U.S. Pat. App. Pub. No. 2014/0261495 to Novak et al., and U.S. Pat. No. 9,220,302 to DePiano et al., all of which are incorporated herein by reference.

In some examples, the control component 208 includes a number of electronic components, and in some examples may be formed on an electronic printed circuit board (PCB) that supports and electrically connects the electronic components. The electronic components may include a microprocessor or processor core, and a memory. In some examples, the control component may include a microcontroller with integrated processor core and memory, and may further include one or more integrated input/output peripherals. In some examples, the control component may be coupled to a communication interface 228 to enable wireless communication with one or more networks, computing devices or other appropriately-enabled devices. Examples of suitable communication interfaces are disclosed in U.S. Pat. App. Pub. No. 2016/0261020 to Marion et al., the content of which is incorporated herein by reference. Another example of a suitable communication interface is the CC3200 single chip wireless microcontroller unit (MCU) from Texas Instruments. And examples of suitable manners according to which the aerosol delivery device may be configured to wirelessly communicate are disclosed in U.S. Pat. App. Pub. No. 2016/0007651 to Ampolini et al., and U.S. Pat. App. Pub. No. 2016/0219933 to Henry, Jr. et al., each of which is incorporated herein by reference.

Figure 3:
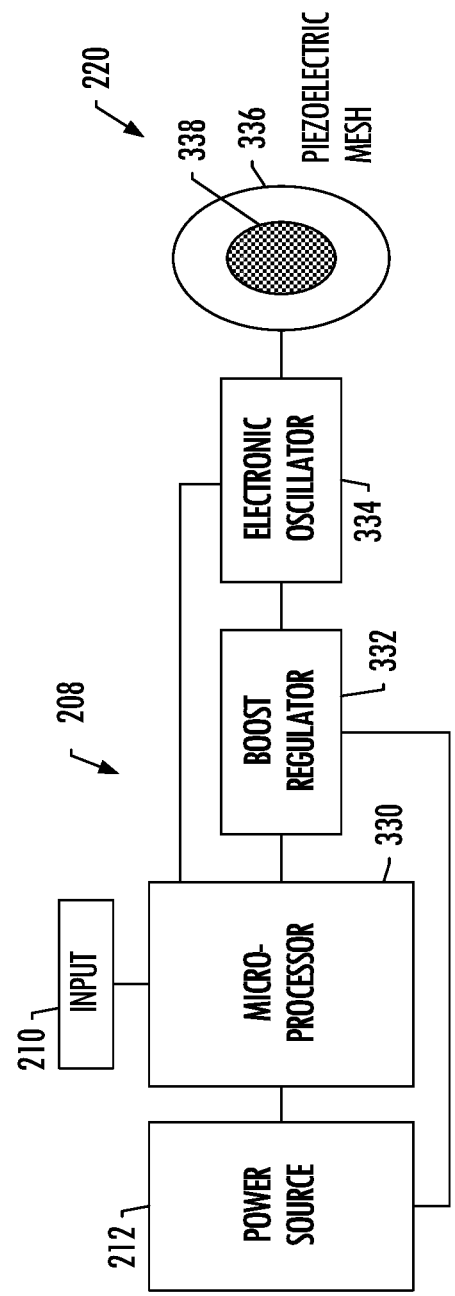
FIGS. 3, 4 and 5 illustrate various elements of the aerosol delivery device according to various example implementations.
Figure 4:
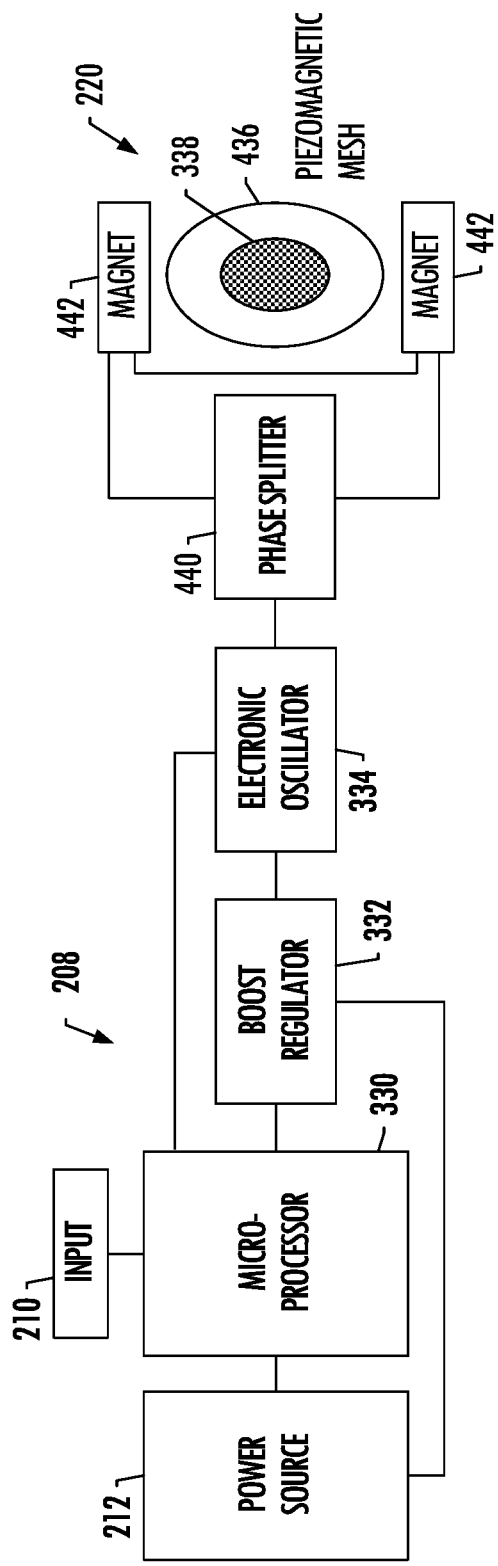

FIGS. 3 and 4 illustrate various elements of the aerosol delivery device 100, according to various example implementations. As shown, the control component 208 may include a microprocessor 330, boost regulator 332 and electronic oscillator 334. In some examples, as shown in FIG. 3, the nozzle 220 includes a piezoelectric material 336 surrounding a mesh 338. In other examples, as shown in FIG. 4, the nozzle includes a piezomagnetic material 436 surrounding a mesh 338, and the control component further includes a phase splitter 440, and a pair of magnets 442 (e.g., permanent magnets, electromagnets) on either side of the piezomagnetic material. In one example, the electronic oscillator and phase splitter may be implemented by a push-pull transformer driver such as the MAX13253 push-pull transformer driver from Maxim Integrated. These and perhaps other electrical components, such as resistors, capacitors, switches and the like, may be coupled with the input device 210 and power source 212 to form an electrical circuit.

In some examples, the power source 212 is a rechargeable battery (e.g., LiB) having a nominal voltage between 3.7 and 4.1 volts. In some examples, a buck-boost converter is connected to the power source 212, between the power source and its load. The buck-boost converter enables sufficient current out of the battery to drive the piezoelectric/piezomagnetic material 336/436 to vibrate, even at voltages down to 2.7 volts. This in turn facilitates use of more output from a single charge of the power source, and greater efficiency for its output. One example of a suitable buck-boost converter is the ADP1614 model step-up, DC-to-DC converter from Analog Devices.

Briefly looking back to FIG. 2, in examples including the micro pump 224, the micro pump is proximate a reservoir side of the mesh 338 to deliver aerosol precursor composition from the reservoir to the mesh for discharge of components thereof. Similarly, in examples including the micro filter 226, the micro filter is proximate a reservoir side of the mesh to filter the aerosol precursor composition delivered from the reservoir to the mesh for discharge of components thereof. And in examples including both the micro pump and micro filter, the micro filter is between the micro pump and the mesh to filter the aerosol precursor composition delivered from the reservoir to the mesh.

Returning to FIGS. 3 and 4, the microprocessor 330 is coupled to and configured to drive the piezoelectric/piezomagnetic material 336/436 to vibrate and cause a discharge of components of aerosol precursor composition (from the reservoir 218) through the mesh 338 and thereby produce an aerosol for inhalation by a user. The aerosol delivery device 100 may therefore produce an aerosol for inhalation without a heater or heating element to heat and thereby volatilize the aerosol precursor to form an aerosol.

According to example implementations of the present disclosure, the components of aerosol precursor composition discharged through the mesh 338 have a diameter of less than one micrometer. In some examples, the piezoelectric/piezomagnetic material 336/436 has a resonant frequency of up to 400 megahertz. In some examples, the piezoelectric or piezomagnetic material has a resonant frequency of 1,000 kilohertz (up to 400 megahertz), and the mesh is a MEMS device. In other examples, the piezoelectric/piezomagnetic material has a resonant frequency of 130 kilohertz (up to 400 megahertz), and the mesh is a stainless steel mesh. And in some examples, the mesh has a curved surface.

The boost regulator 332 is between the power source 212 and an electrical load that includes the piezoelectric/piezomagnetic material 336/436. The boost regulator is configured to step up the voltage output of the power source to a higher voltage, and the microprocessor 330 is configured to drive the boost regulator to output the higher voltage to power the piezoelectric/piezomagnetic to vibrate.

The electronic oscillator 334 is coupled to and between the microprocessor 330 and piezoelectric/piezomagnetic material 336/436, and the microprocessor is configured to drive the electronic oscillator to produce a periodic, oscillating electronic signal to drive the piezoelectric/piezomagnetic material at a resonant frequency thereof. In some examples, the microprocessor is configured to output a pulsing signal to drive the electronic oscillator to produce the periodic, oscillating electronic signal, with the pulsing signal having a programmable duty cycle. The frequency of the periodic, oscillating electronic signal depends on the duty cycle, and by programming the duty cycle, the frequency periodic, oscillating electronic signal may likewise be programmed to allow use of piezoelectric/piezomagnetic materials with different resonant frequencies. In some examples, the microprocessor is configured to control the electronic oscillator to produce the periodic, oscillating electronic signal having a frequency of 1,000 kilohertz (up to 400 megahertz) that corresponds to the resonant frequency of the piezoelectric/piezomagnetic material.

In some examples, as shown in FIG. 3, the electronic oscillator 334 is electrically coupled to piezoelectric material 336 and configured to produce the periodic, oscillating electronic signal to drive the piezoelectric material to vibrate. In other examples, as shown in FIG. 4, the phase splitter 440 configured to receive the periodic, oscillating electronic signal from the electronic oscillator and produce a pair of periodic, oscillating electronic signals that are antiphase (i.e., 180 degrees apart). In these other examples, the phase splitter is configured to produce the pair of periodic, oscillating electronic signals to drive the pair of magnets 442 to produce periodic, oscillating magnetic fields that are antiphase and thereby drive the piezomagnetic material 436 to vibrate.

In examples including both the boost regulator 332 and the electronic oscillator 334, the electronic oscillator is coupled to and between the boost regulator and piezoelectric/piezomagnetic material 336/436. In these examples, the microprocessor 330 is configured to drive the boost regulator to output the higher voltage to power the electronic oscillator to produce a periodic, oscillating electronic signal to drive the piezoelectric/piezomagnetic material to vibrate at a resonant frequency thereof. In some examples, the microprocessor is configured to output a pulsing signal to drive the boost regular and thereby the electronic oscillator to produce the periodic, oscillating electronic signal, with the pulsing signal having a programmable duty cycle. And in some examples, the microprocessor is configured to control the electronic oscillator to produce the periodic, oscillating electronic signal having a frequency of 1,000 kilohertz (up to 400 megahertz) that corresponds to the resonant frequency of the piezoelectric/piezomagnetic material.

Figure 5:
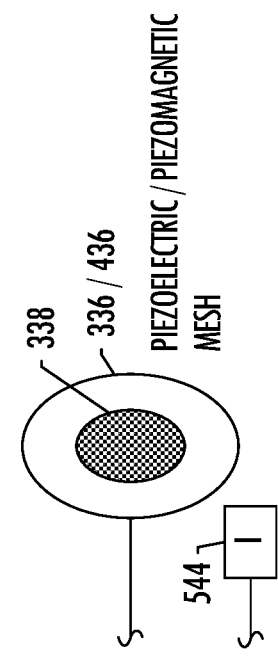

In some examples, as shown in FIG. 5, the control component 208 further includes a current sensor 544 configured to measure electric current through the piezoelectric/piezomagnetic material 336/436. In the case of the piezomagnetic material, an additional electric current provided to the material, such as from the microprocessor 330 through an additional resistor to limit the additional electric current. Examples of suitable current sensors include current-sense resistors, Hall effect current sensors and the like. In these examples, the current sensor may be connected to the microprocessor, which may be configured to control at least one functional element of the aerosol delivery device 100 based on the measured electric current. In at least some examples, the microprocessor may be configured to cut off the power supply in an instance in which the electric current is above or below a threshold level indicative of a defective nozzle 220.

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIGS. 1-3 or as otherwise described above may be included in an aerosol delivery device according to the present disclosure.

Many modifications and other implementations of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific implementations disclosed, and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. An aerosol delivery device comprising:
    at least one housing enclosing a reservoir configured to retain an aerosol precursor composition;
    an opening defined in the housing;
    a piezoelectric or piezomagnetic material;
    a control component including a microprocessor coupled to and configured to drive the piezoelectric or piezomagnetic material to vibrate and cause a discharge of components of the aerosol precursor composition to thereby produce an aerosol; and
    a transport element configured to deliver an amount of aerosol precursor composition from the reservoir to the piezoelectric or piezomagnetic material.

2. The aerosol delivery device of claim 1, wherein the aerosol is configured to be whisked, aspirated, or otherwise drawn away through the opening.

3. The aerosol delivery device of claim 1, wherein the transport element comprises a micro pump configured to deliver aerosol precursor composition from the reservoir.

4. The aerosol delivery device of claim 1, wherein the transport element is positioned proximate a reservoir side of the piezoelectric or piezomagnetic material.

5. The aerosol delivery device of claim 4, wherein the aerosol delivery device further comprises a micro filter configured to filter the aerosol precursor composition delivered from the reservoir.

6. The aerosol delivery device of claim 1, wherein the control component further includes an electronic oscillator coupled to and between the microprocessor and piezoelectric or piezomagnetic material, and
    wherein the microprocessor being configured to drive the piezoelectric or piezomagnetic material includes being configured to drive the electronic oscillator to produce a periodic, oscillating electronic signal to drive the piezoelectric or piezomagnetic material at a resonant frequency thereof.

7. The aerosol delivery device of claim 6, wherein the microprocessor is configured to output a pulsing signal to drive the electronic oscillator to produce the periodic, oscillating electronic signal, the pulsing signal having a programmable duty cycle.

8. The aerosol delivery device of claim 6, wherein the microprocessor is configured to control the electronic oscillator to produce the periodic, oscillating electronic signal having a frequency of 1,000 kilohertz that corresponds to the resonant frequency of the piezoelectric or piezomagnetic material.

9. The aerosol delivery device of claim 6, wherein the piezoelectric or piezomagnetic material is piezoelectric material, and the electronic oscillator is electrically coupled to the piezoelectric material and configured to produce the periodic, oscillating electronic signal to drive the piezoelectric material to vibrate.

10. The aerosol delivery device of claim 6, wherein the piezoelectric or piezomagnetic material is piezomagnetic material, and the control component further includes:
    a pair of magnets on either side of the piezomagnetic material; and
    a phase splitter configured to receive the periodic, oscillating electronic signal and produce a pair of periodic, oscillating electronic signals that are antiphase, the phase splitter being configured to produce the pair of periodic, oscillating electronic signals to drive the pair of magnets to produce periodic, oscillating magnetic fields that are antiphase and thereby drive the piezomagnetic material to vibrate.

11. The aerosol delivery device of claim 1 further comprising a current sensor configured to measure electric current through the piezoelectric or piezomagnetic material, wherein the microprocessor is configured to control operation of at least one functional element of the aerosol delivery device in response to the electric current so measured.

12. The aerosol delivery device of claim 1, wherein the piezoelectric or piezomagnetic material surrounds a mesh.

13. The aerosol delivery device of claim 12, wherein the mesh has a curved surface.

\* \* \* \* \*